US010266460B2

(12) United States Patent
Colling

(10) Patent No.: US 10,266,460 B2
(45) Date of Patent: Apr. 23, 2019

(54) ENHANCED HEAT RECOVERY IN PARAXYLENE PLANT

(71) Applicant: BP Corporation North America Inc., Houston, TX (US)

(72) Inventor: Craig Colling, Warrenville, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/105,681

(22) PCT Filed: Dec. 10, 2014

(86) PCT No.: PCT/US2014/069549
§ 371 (c)(1),
(2) Date: Jun. 17, 2016

(87) PCT Pub. No.: WO2015/094857
PCT Pub. Date: Jun. 25, 2015

(65) Prior Publication Data
US 2016/0318831 A1 Nov. 3, 2016

Related U.S. Application Data

(60) Provisional application No. 61/917,061, filed on Dec. 17, 2013.

(51) Int. Cl.
*C07C 7/04* (2006.01)
*C07C 7/00* (2006.01)
*B01D 3/00* (2006.01)
*C07C 7/14* (2006.01)
*B01D 3/32* (2006.01)
*B01D 9/00* (2006.01)

(52) U.S. Cl.
CPC .............. *C07C 7/005* (2013.01); *B01D 3/007* (2013.01); *B01D 3/322* (2013.01); *B01D 9/0031* (2013.01); *C07C 7/04* (2013.01); *C07C 7/14* (2013.01); *Y02P 20/51* (2015.11); *Y02P 20/57* (2015.11); *Y02P 70/34* (2015.11)

(58) Field of Classification Search
None
See application file for complete search history.

(56) References Cited

U.S. PATENT DOCUMENTS 2,773,918 A * 12/1956 Stephens .................. C07C 7/10
203/27
3,037,062 A * 5/1962 Gerhold .................. C07C 7/10
203/73

(Continued)

FOREIGN PATENT DOCUMENTS

GB          694980 A       7/1953
JP        S49-019268       5/1974
(Continued)

*Primary Examiner* — Tam M Nguyen
(74) *Attorney, Agent, or Firm* — Robert N. Carpenter

(57) ABSTRACT

Processes and apparatuses for enhanced heat recover}/in a paraxylene manufacturing plant use a side condenser to recover high quality heat. By placing the side condenser below the location of a feed stream comprising low molecular weight gases, the heat recovered is free of such non-condensable gases. Such gases are undesirable when using the condensed vapor in other applications.

11 Claims, 1 Drawing Sheet

(56) References Cited

U.S. PATENT DOCUMENTS

| | | | | |
|---|---|---|---|---|
| 3,198,846 | A | * | 8/1965 | Kelso .................. C07C 4/16 208/216 R |
| 3,399,227 | A | * | 8/1968 | Tapulionis .............. C07C 67/54 560/78 |
| 3,522,153 | A | | 7/1970 | King |
| 3,584,068 | A | * | 6/1971 | Murray Goger et al. .................. C07C 5/2708 203/25 |
| 3,855,077 | A | * | 12/1974 | Bieser .................... B01D 3/14 203/14 |
| 4,381,419 | A | | 4/1983 | Wylie |
| 4,664,786 | A | | 5/1987 | Forte et al. |
| 5,310,480 | A | * | 5/1994 | Vidueira .................. C10G 7/08 208/313 |
| 5,336,840 | A | | 8/1994 | Forte |
| 6,240,744 | B1 | * | 6/2001 | Agrawal .................. B01D 3/14 62/643 |
| 2008/0293981 | A1 | | 11/2008 | Schultz et al. |
| 2014/0142364 | A1 | * | 5/2014 | Io .............................. B01D 3/14 585/805 |
| 2014/0224637 | A1 | * | 8/2014 | Bhargava ............... B01D 3/007 202/154 |

FOREIGN PATENT DOCUMENTS

| | | |
|---|---|---|
| JP | S48-038274 | 9/1974 |
| SU | 358927 A1 | 9/1996 |
| SU | 1032726 A1 | 9/1996 |
| WO | WO 2012/173755 | 12/2012 |

* cited by examiner

ENHANCED HEAT RECOVERY IN PARAXYLENE PLANT

CROSS-REFERENCE TO RELATED APPLICATION

This application claims priority to U.S. Provisional Application No. 61/917,061, filed Dec. 17, 2013, which is hereby incorporated by reference in its entirety.

FIELD

This disclosure relates to processes and apparatuses for enhanced heat recovery during the manufacture of paraxylene. Such processes and apparatuses include a side condenser located at a position such that the liquid formed from the condensed vapor is free of non-condensable low molecular weight gases.

BACKGROUND

Paraxylene is used in the manufacture of polyester which is useful as fibers and polymeric resins. Paraxylene can be manufactured from several feedstocks, the most significant today being reformate produced from naphtha reforming. The two primary processes used to manufacture paraxylene use crystallization or selective adsorption.

Both types of paraxylene manufacturing plants employ heat in the reboiler(s) of a distillation or fractionation tower(s) to separate the tower feed(s) into useful products, including paraxylene. Feed(s) to the tower may come from multiple sources and enter the tower(s) at various locations. The product of fractionation is a stream containing predominantly the xylene isomers including paraxylene that is sent to the crystallization selective adsorption section to recover paraxylene. Crystallization is much less sensitive to impurities in the fractionation product stream than selective adsorption, where these impurities can lead to manufacturing difficulties. Consequently the fractionation employed in crystallization can employ a single tower where the fractionation product stream can be removed as a side stream.

In both processes, the heat needed to drive fractionation is typically supplied in the reboiler, either in a fired heater or via heat exchange with steam, and removed in a condenser with the tower overhead product, typically via air and/or cooling water-cooling. If the fractionation tower operates at close to ambient conditions, the heat removed in the overhead condenser is often too low in temperature or thermodynamic quality to be useful. Both types of paraxylene manufacturing processes can raise the pressure of the fractionation tower so that the temperature or thermodynamic quality of the heat removed in the overhead condenser is higher and useful in other parts of the paraxylene manufacturing plant. However raising the tower pressure increases the cost of the fractionation equipment and lowers the separation efficiency. Thus, there is a need to recover heat in the fractionation employed in paraxylene manufacturing without raising tower pressure to increase the temperature or thermodynamic quality of the heat.

Side condensers located below the overhead condenser on the fractionation tower(s) can remove the heat at higher temperature. It is important to note that the feed to the fractionation tower(s) of paraxylene manufacturing plants often contain low molecular weight gases. One disadvantage of side condensers is that the heat removed by condensing the tower side condenser product contains low molecular weight gases. There are problems associated with the flashing of these low molecular weight gases if side condensers are employed. Thus, there is a need for a process and apparatus to effectively recover heat free of low molecular weight gases in a paraxylene manufacturing process.

BRIEF SUMMARY

In one aspect, a process for recovering heat in a paraxylene manufacturing plant is provided, the process comprising: providing at least a first feed stream to a fractionation tower; supplying heat to a reboiler of the fractionation tower to separate the feed stream into an overhead vapor product, an overhead liquid product, a bottoms product, and a sidedraw product comprising xylenes; and recovering heat with a side condenser, wherein the side condenser is located below the first feed stream.

In another aspect, a process for recovering heat in a paraxylene manufacturing plant is provided, the process comprising: providing a first feed stream and a second feed stream to a fractionation tower, wherein the first feed stream is provided through a low temperature separator input and the second feed stream is provided through a high temperature separator input; and supplying heat to a reboiler of the fractionation tower to separate the first and second feed streams into an overhead vapor product, an overhead liquid product, a bottoms product, and a sidedraw product. The process further comprises supplying the sidedraw product to a paraxylene recovery section; and recovering heat with a side condenser, wherein the side condenser is located between one and ten trays below the second feed stream.

In yet another aspect, an apparatus for recovering heat in a paraxylene manufacturing plant is provided, the apparatus comprising: a low temperature separator unit for providing a first feed stream to a fractionation tower; a high temperature separator unit for providing a second feed stream to the fractionation tower, wherein the fractionation tower separates the first and second feed streams into an overhead vapor product, an overhead liquid product, a bottoms product, and a sidedraw product; and a side condenser for recovering heat, wherein the side condenser is located below the second feed stream.

DETAILED DESCRIPTION

The present disclosure provides processes and apparatuses for using a side condenser to recover heat at a location between the reboiler and the overhead condenser in a fractionation tower of a paraxylene manufacturing plant. This results in heat recovery at a higher temperature, producing higher quality heat that can be used elsewhere in the petrochemical plant or refinery. This has significant energy efficiency advantages over the prior art because low quality heat that was previously rejected to air and/or water is now recovered at a higher quality such that it is useful for other applications.

Figure 1:
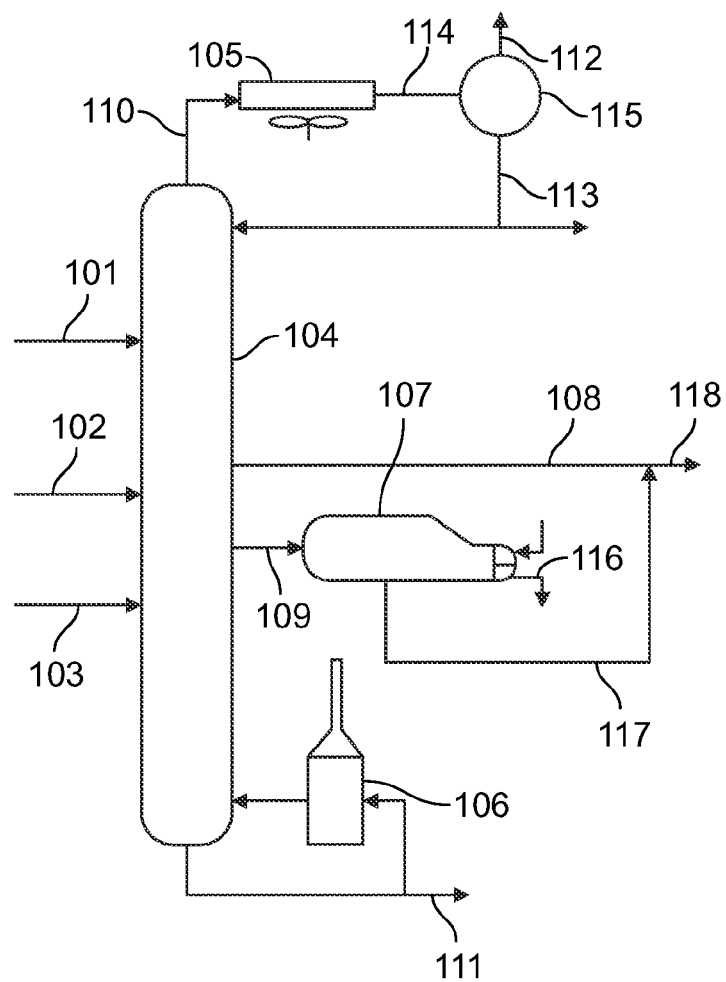
FIG. 1 is an apparatus for producing paraxylene comprising a side condenser.

FIG. 1 shows an apparatus for producing paraxylene having enhanced heat recovery. A first feed stream 101, a second feed stream 102, and a third feed stream 103 may be provided to fractionation tower 104. The first feed stream 101 may be provided through a low temperature separator unit and the second feed stream 102 may be provided through a high temperature separator unit. The first feed stream 101 and the second feed stream 102 may comprise xylenes, low molecular weight gases, and heavy aromatics. For example, the first feed stream 101 and the second feed stream 102 may comprise between about 80 and 90 percent C8 aromatics, between about 5 and 10 percent benzene and toluene, and between about 5 and 10 percent C9+ aromatics, such as trimethylbenzene and methylethyl benzene. Those skilled in the art will appreciate that the designator "CX" refers to a compound comprising X carbon atoms, "CX+" refers to a compound comprising X or greater carbon atoms, and "CX–" refers to a compound comprising X or fewer carbon atoms. There are three isomers of xylenes: orthoxylene (oX), metaxylene (mX), and paraxylene (pX). C8 aromatics comprise the three xylene isomers and ethylbenzene (EB).

The first feed stream 101 may be at a temperature of between about 125 to 175 degrees Celsius, preferably about 150 degrees Celsius. The second feed stream 102 may be at a temperature of greater than 175 degrees Celsius, preferably about 200 degrees Celsius. The third feed stream 103 is the feed stream to the paraxylene manufacturing plant. This stream can be comprised of several sources, typically heavy reformats from a naphtha. reformer and toluene column bottoms from a transalkylation unit. See, e.g., "Handbook of Petroleum Refining Processes", R. A. Meyers, ed., Mc-Graw-Hill, 2004, Stream 103 may comprise about 60 percent C8 aromatics and about 40 percent C9+ aromatics and may be at temperature between about 200 and 250 degrees Celsius, preferably about 230 degrees Celsius.

The fractionation tower 104 may comprise a plurality of trays, an overhead condenser 105, a reboiler 106, and a side condenser 107. The fractionation tower 104 may produce a liquid sidedraw product 108, a vapor sidedraw product 109, an overhead product 110, and a bottom product 111. The liquid sidedraw product 108 and the vapor sidedraw product 109 may comprise xylenes, such as paraxylene. The liquid sidedraw product 108 and the vapor sidedraw product 109 may also comprise small amounts of toluene and C9 aromatics. In some embodiments, the liquid sidedraw product 108 and the vapor sidedraw product 109 may comprise about between about 90 and about 98 percent C8 aromatics (mixed xylenes). The overhead product 110 may be separated into an overhead vapor product 112 and an overhead liquid product 113. The overhead vapor product 112 may comprise benzene, hydrogen, ethane, and other light hydrocarbon gases. The overhead vapor product 112 may be provided to the reboiler 106 as fuel. The overhead liquid product 113 may comprise benzene, toluene, and C8 aromatics. The bottoms product 111 may comprise heavy aromatics, such as C9+ aromatics. The overhead product 110 may be at a temperature of between about 110 and 150 degrees Celsius, preferably at about 130 degrees Celsius. The bottoms product 111 may be at a temperature of between about 210 and 260 degrees Celsius, preferably at about 240 degrees Celsius.

The overhead product 110 may be condensed in the overhead condenser 105 to produce a condensed overhead product 114. The condensed overhead product 114 may be provided to a vapor-liquid separator 115 to produce the overhead vapor product 112 and the overhead liquid product 113. The overhead condenser 105 may have a duty of less than about 35 Mmkcal/h, preferably less than 20 Mmkcal/h. The side condenser 107 may recover heal in the vapor sidedraw product 109. The first feed stream 101 may be located above the second feed stream 102, which may be located above the third feed stream 103. The side condenser 107 may be located below the first feed stream 101. For example, the side condenser 107 may be located between the second feed stream 102 and the third feed stream 103, preferably between one and ten trays below the second feed stream 102, more preferably between one and five trays below the second feed stream 102. When the second feed stream 102 comes from the high temperature separator unit, it may contain residual amounts of low molecular weight gases, such as non-condensable hydrocarbons (e.g., hydrogen, ethane). By placing the side condenser 107 below the second feed stream, these low molecular weight gases will not be present in the vapor sidedraw product 109. This allows heat to be recovered in the side condenser without forming a vapor product, thereby avoiding expensive compression costs or wasteful venting.

The heat 116 recovered with the side condenser 107 may be at a temperature of less than about 200 degrees Celsius. In alternative embodiments, the heat 116 recovered with the side condenser 107 may be at a temperature f between about 190 and 210 degrees Celsius. In recovering the heat 116, the side condenser 107 condenses the vapor sidedraw product 109 to form a condensed liquid sidedraw product 117, which may be combined with the liquid sidedraw product 108 to produce a combined sidedraw product 118. The heat 116 may be used in any process that is upstream of the paraxylene process, for example other locations in the aromatics complex, petrochemical facility, or petroleum refinery. For example, if the paraxylene manufacturing plant is located in an aromatics complex, the heat 116 would be suitable to supply heat to the reformats splitter or toluene column. See, e.g., "Handbook of Petroleum Refining Processes", R. A. Meyers, ed., Mc-Graw-Hill, 2004. Alternatively the heat 116 could be used to make steam. This steam could be used in a nearby facility or community for heating. In addition, this steam could be used to drive an expander and make electrical power. The combined sidedraw product 118 may be provided to a paraxylene recovery section in order to recover paraxylene. The paraxylene recovery section may comprise a crystallization unit.

Figure 2:
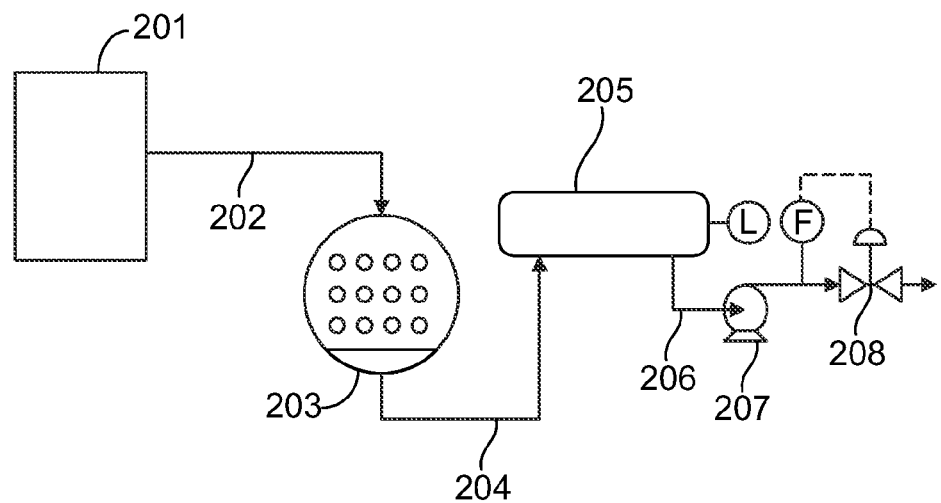
FIG. 2 is a side condenser in an apparatus for producing paraxylene.

FIG. 2 illustrates a side condenser of the present disclosure. A fractionation column 201 provides a vapor sidedraw stream 202 to a side condenser 203. The side condenser 203 may produce a first condensed sidedraw stream 204 and useful heat. The first condensed sidedraw stream 204 may be provided to a condensate drum 205 to produce a condensed sidedraw stream 206. The condensed sidedraw stream 206 may be pumped through pump 207 and first flow control valve 208 to a paraxylene recovery section.

Various condenser systems may be used to control the pressure in the fractionation column 201. Examples include a flooded condenser system, a hot-vapor bypass system, and a cooling-water throttling system. See, e.g., Lieberman, N. P. and Lieberman E. T., "A Working Guide to Process Equipment", McGraw-Hill 1997. The pressure is dependent on the surface area of the side condenser 203 exposed to the saturated vapor from sidedraw stream 202, in a flooded condenser system, the condensate drum 205 is run full, i.e., the flow from the reflex pump 207 is restricted, thus increasing the level in the side condenser 203, reducing the heat-transfer surface area available for condensation, and raising the fractionation column 201 pressure.

EXAMPLES

Simulation results from Aspen Plus computer simulations of a paraxylene unit are shown in Examples 1 and 2 below.

Example 1: Impact of Increasing Vapor Sidedraw Flow Rate on Duties, Temperatures, and Concentrations This example shows the effect of increasing the vapor sidedraw flow rate on condenser and reboiler duties, the condensing temperature, and the toluene concentration in the liquid sidedraw. Results are shown in Table 1 below. For the base simulation, the condenser and reboiler duties of the xylene recovery column are about 34.6 and 55.9 Mmkcal/hr, respectively. Simulation numbers 1, 2, and 3 use increasing vapor flow rates for the sidedraw condenser. As the vapor flow rate increases, the vapor sidedraw condenser duty increases, which provides useful work. In addition, the column overhead condenser duty decreases, saving energy. As the vapor flow rate increases, the column reboiler duty and the toluene concentration increase only slightly. Vapor does not go to the top of the column where the toluene is removed. There are limits to how much heat can be removed. It was surprising that a large quantity of heat could be removed from the column and turned into useful work without significantly increasing the column reboiler duty and toluene concentration in the liquid sidedraw.

eliminate this increase in reboiler duty, but increasing the number of stages increases capital costs. It was not expected that it would be possible to remove the sidedraw vapor with very little increase on the reboiler duty because it was expected that many more stages would be needed below where feed stream 102 enters the column for the concentration of low molecular weight gases in the vapor phase to be low enough.

This example also shows that the amount of C9+ material in the liquid sidedraw increases as vapor is removed further down the column. Again, this is because removing vapor from further down the column provides fewer stages to perform the separation at the bottom of the column. Thus, more C9+ is carried overhead. The concentrations of C9+ below are acceptable for a crystallization based paraxylene process. Concentrations above about 2.4 weight percent C9+ will significantly increase capital and operating cost of the paraxylene plant. It is important to note that selective adsorption based paraxylene processes cannot tolerate these levels of C9+ aromatics in the feed to the crystallization section.

TABLE 1

Impact of Increasing Vapor Sidedraw Flow Rate on Duties, Temperatures, and Concentrations

|  | Vapor Flow Rate Through Vapor Sidedraw Condenser, lb/hr (kg/hr) | Vapor Sidedraw Condenser Duty, Mmkcal/h | Column Overhead Condenser Duty, Mmkcal/h | Column Reboiler Duty Reboiler Duty, Mmkcal/h | Vapor Sidedraw Condensing Temperature, °C. | Toluene Concentration in Liquid Sidedraw, wt % |
|---|---|---|---|---|---|---|
| Base | 1 (0.45) | 1.00E−05 | 34.6 | 55.9 | 197.5 | 0.6 |
| 1 | 5000 (2268) | 0.17 | 34.4 | 55.9 | 197.5 | 0.6 |
| 2 | 50000 (22678) | 1.72 | 32.9 | 55.9 | 197.4 | 0.6 |
| 3 | 500000 (226796) | 17.2 | 18.4 | 56.2 | 197.1 | 1.2 |

Example 2: Impacting of Lowering Vapor Sidedraw Removal Location on Condensing Temperature, Reboiler Duty, and Sidedraw Composition This example shows the effect of the location of the sidedraw on vapor sidedraw temperature, column reboiler duty, and liquid sidedraw composition. The total number column stages is kept constant in each simulation. Results are shown in Table 2 below. These results start at two stages below where feed stream 102 enters the column. It was very surprising that the concentration of low molecular weight gases in the vapor phase was so low only two stages below where feed stream 102 enters the column. When the sidedraw is located further down in the column (i.e., at more stages below the sidedraw and the feed stream coming from the high temperature separator), the temperature increases, which improves the quality of the heat available. However, this also increases the column reboiler duty because removing vapor from further down the column provides fewer stages to perform the separation at the bottom of the column. It may also be possible to increase the number of stages and

TABLE 2

Impact of Lowering Vapor Sidedraw Removal Location on Condensing Temperature, Reboiler Duty, and Sidedraw Composition

| Number of Stages Below Feed Stream 102 Where Vapor is Removed | Vapor Sidedraw Condensing Temperature, °C. | Column Reboiler Duty Reboiler Duty, Mmkcal/h | C9+ Concentration in Liquid Sidedraw, wt % |
|---|---|---|---|
| 2 | 202 | 70.92 | 2.4 |
| 12 | 205 | 72.86 | 4.0 |
| 22 | 214 | 81.19 | 13 |

What is claimed is:
1. A process for recovering heat in a paraxylene manufacturing plant, the process comprising:
   providing a first feed stream to a fractionation tower, wherein the feed stream comprises C8 aromatics;
   supplying heat to a reboiler of the fractionation tower to separate the feed stream into an overhead product comprising benzene, a bottoms product comprising C9+ aromatics, a liquid sidedraw product comprising xylene recovered through a liquid sidedraw outlet and a vapor sidedraw product comprising xylenes recovered though a vapor sidedraw outlet; and recovering heat from the vapor sidedraw product with a side condenser, wherein the vapor sidedraw outlet is located below the first feed stream.

2. The process of claim 1, further comprising providing a second feed stream and a third feed stream to the fractionation tower.

3. The process of claim 2, wherein the vapor sidedraw outlet is located between the second feed stream and the third feed stream.

4. The process of claim 2, wherein the vapor sidedraw outlet is located between one and ten trays below the second feed stream.

5. The process of claim 1 wherein the heat recovered with the side condenser is at a temperature of less than 200 degrees Celsius.

6. The process of claim 1, wherein the heat recovered with the side condenser is at a temperature of between about 190 and 210 degrees Celsius.

7. The process of claim 1, wherein the sidedraw product comprises about 90 to about 98 percent C8 aromatics.

8. The process of claim 1, further comprising supplying the sidedraw product to a paraxylene recovery section.

9. The process of claim 8, wherein the paraxylene recovery section comprises a crystallization unit.

10. The process of claim 1, further comprising condensing the vaper sidedraw product in the condenser to form a condensate.

11. The process of claim 10 wherein the condensate and the liquid sidedraw product are combined to form a combined sidedraw product.

* * * * *